United States Patent [19]

Ueda et al.

[11] Patent Number: 4,701,325
[45] Date of Patent: Oct. 20, 1987

[54] INJECTABLE AQUEOUS SOLUTION CONTAINING HYDROGENSULFITE AND/OR SULFITE AND ANTICANCEROUS BENZODIAZEPINE COMPOUND

[75] Inventors: Yasuo Ueda, Hirakata; Yoshio Kagitani, Kashihara; Shirou Komeda, Tondabayashi, all of Japan; Satoshi Funakoshi, Los Angeles, Calif.

[73] Assignee: The Green Cross Corporation, Osaka, Japan

[21] Appl. No.: 580,183

[22] Filed: Feb. 15, 1984

[30] Foreign Application Priority Data

Feb. 17, 1983 [JP] Japan ................. 58-25996

[51] Int. Cl.$^4$ ................. A61K 33/04; A61K 31/55
[52] U.S. Cl. ................. 424/164; 514/220
[58] Field of Search ................. 424/164, 274; 514/220

[56] References Cited

U.S. PATENT DOCUMENTS 4,309,437   1/1982   Ueda et al. ................. 424/274

OTHER PUBLICATIONS

Dyer, An Index of Tumor Chemotherapy, 1949, WIH, p. 37.

*Primary Examiner*—Jerome D. Goldberg
*Attorney, Agent, or Firm*—Cushman, Darby & Cushman

[57] ABSTRACT

An alkali metal hydrogensulfite or sulfite is effective for controlling a local injury such as inflammation and vein injury occurring on the injection of an antitumor benzodiazepine compound of the formula

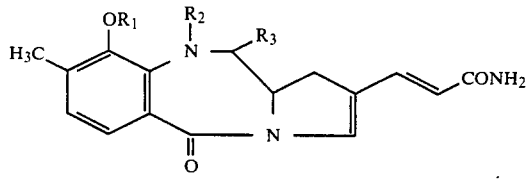

wherein $R_1$ denotes hydrogen atom, or acyl, carbamyl, or alkoxycarbonyl group; $R_2$ denotes hydrogen atom or acyl group; and $R_3$ denotes sulfinic acid rest, $SO_2X$, or sulfonic acid rest, $SO_3X$, X meaning hydrogen, alkali metal or alkaline earth metal. An aqueous solution containing the both can be administered by injection.

7 Claims, 1 Drawing Figure

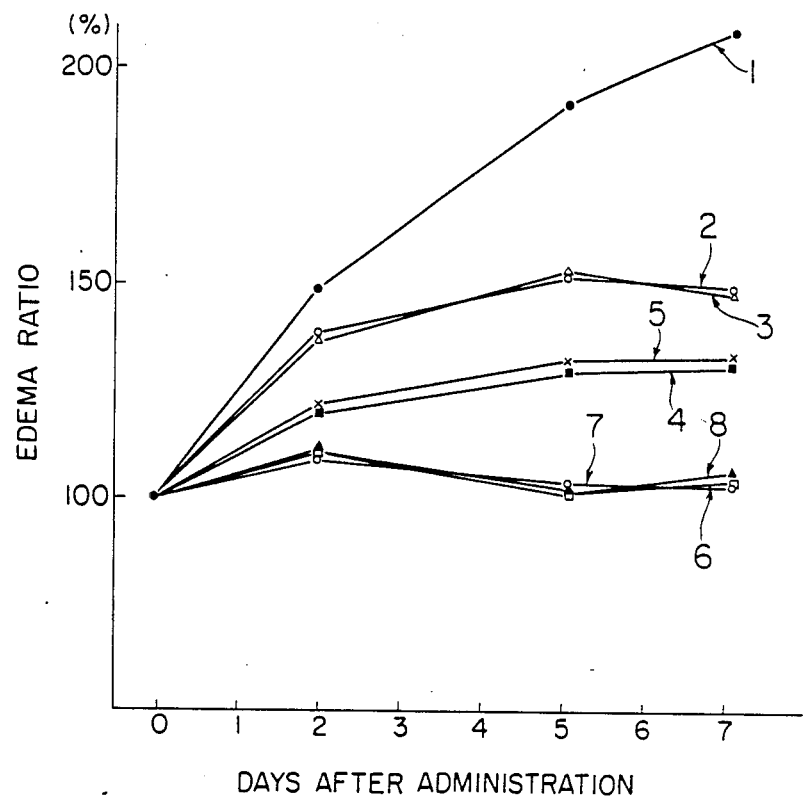

INJECTABLE AQUEOUS SOLUTION CONTAINING HYDROGENSULFITE AND/OR SULFITE AND ANTICANCEROUS BENZODIAZEPINE COMPOUND

This invention relates to the prevention of a local-injury caused on the injection administration of a medicine which causes local-injury.

Nowadays, various compounds are used practically as a medicine or proposed as such. Of not a few of these, however, their improvement is eagerly waited for or their practical utilization is being left over. This is due to their property to cause a local injury, for example, a property to cause, when they are injected subcutaneously or they leak out of the blood vessel after being injected intravenously, an inflammation at the local region, or to cause injury in the blood vessel when intravenously injected continually.

For example, some of the benzodiazepine compounds have been widely studied and developed as a carcinostatic or antibacterial agent. Also some of the present inventors have previously provided as a carcinostatic agent 1H-pyrrolo[2,1-c][1,4]benzodiazepin-2-acrylamide compound represented by the formula

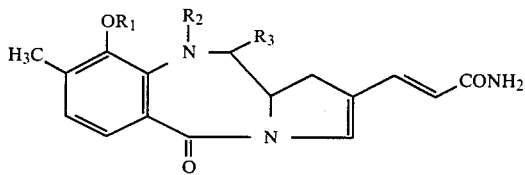

wherein $R_1$ denotes a hydrogen atom, or acyl, carbamyl or alkoxycarbonyl group; $R_2$ denotes a hydrogen atom or acyl group, and $R_3$ denotes sulfinic acid rest, $SO_2X$, or sulfonic acid rest, $SO_3X$, X meaning hydrogen, alkali metal such as sodium and potassium, or alkaline earth metal such as calcium [Japanese Patent Application "Kokai" (Laid-open) No. 15289/81, U.S. Pat. No. 4,309,437 and German Patent No. 3,010,544)].

On subsequent studies, however, it was confirmed that also the benzodiazepine compound, when leaked out of the blood vessel on administration to a living body, was accompanied by a considerably serious inflammation, resulting to a necrosis.

Thus, the object of this invention is to provide a medicine capable of controlling the local injuries as mentioned above. The invention has been accomplished based on the following knowledge.

Namely, the inventors have obtained a novel knowledge that, when a compound having a property to cause a local injury, such as the benzodiazepine compound mentioned above, is administered jointly with a hydrogensulfite or a sulfite, the local injury occuring on subcutaneous or intraperitoneal administration is controlled and also the local injury of blood vessel occurring on continual intravenous administration is controlled.

According to the invention, there is provided an injectable aqueous solution containing a physiologically acceptable metal hydrogensulfite and/or sulfite and an effective amount for controlling tumor of a benzodiazepine compound of the formula

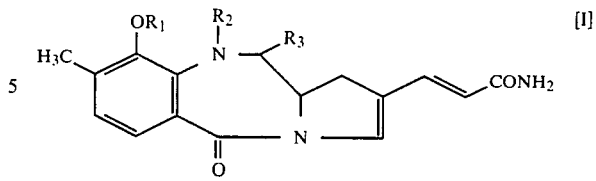

wherein $R_1$ denotes hydrogen atom, or acyl, carbamyl or alkoxycarbonyl group; $R_2$ denotes hydrogen atom or acyl group; and $R_3$ denoes sulfinic acid rest, $SO_2X$, or sulfonic acid rest, $SO_3X$, X meaning hydrogen, alkali metal or alkaline earth metal, the amount of the hydrogensulfite and/or sulfite being 5-15 times the amount of the benzodiazepine compound.

Preferred examples of the physiologically acceptable metal salts of the hydrogensulfite and sulfite used in this invention include alkali metal salts such as the sodium or potassium salt. Of these, particularly preferred are sodium hydrogensulfite and sodium sulfite.

In the benzoazepine compound represent by the formula [I] compound, acyl is benzoyl or alkanoyl having 1 to 6 carbon atoms; carbamyl may have its nitrogen atom substituted with a phenyl group or an alkyl group containing 1 to 6 carbon atoms; and alkoxycarbonyl contains alkoxy group having 1 to 6 carbon atoms.

Examples of the benzodiazepine compounds used in the invention are given below.

5,10,11,11a-Tetrahydro-10-acetyl-9-hydroxy-8-methyl-5-oxo-11-sulfo-1H-pyrrolo[2,1-c][1,4]benzodiazepin-2-acrylamine and alkali metal salts or alkaline eath metal salts thereof.

5,10,11,11a-Tetrahydro-9-acetoxy-10-acetyl-8-methyl-5-oxo-11-sulfo-1H-pyrrolo[2,1-c][1,4]benzodiazepin-2-acrylamide and alkali metal salts or alkaline earth metal salts thereof.

5,10,11,11a-Tetrahydro-10-acetyl-9-carbamyloxy-8-methyl-5-oxo-11-sulfo-1H-pyrrolo[2,1-c][1,4]benzodiazepin-2-acrylamide and alkali metal salts or alkaline earth metal salts thereof.

5,10,11,11a-Tetrahydro-9-hydroxy-8-methyl-5-oxo-11-sulfo-1H-pyrrolo[2,1-c][1,4]benzodiazepin-2-acrylamide and alkali metal salts or alkaline earth metal salts thereof.

5,10,11,11a-Tetrahydro-9-acetoxy-8-methyl-5-oxo-11-sulfo-1H-pyrrolo[2,1-c][1,4]benzodiazepin-2-acrylamide and alkali metal salts or alkaline earth metal salts thereof.

5,10,11,11a-Tetrahydro-9carbamyloxy-8-methyl-5-oxo11-sulfo-1H-pyrrolo[2,1-c][1,4]benzodiazepin-2-acrylamide and alkali etal salts or alkaline earth metal salts thereof.

5,10,11,11a-Tetrahydro-10-acetyl-9-hydroxy-8-methyl-5-oxo-11-sulfino-1H-pyrolo[2,1-c][1,4]benzodiazepin-2-acrylamide and alkali metal salts or alkaline earth metal saltsl thereof.

5,10,11,11a-Tetrahydro-9-acetoxy-10-acetyl-8-methyl-5-oxo-11-sulfino-1H-pyrrolo[2,1-c][1,4]benzodiazepin-2-acrylamide and alkali metal salts or alkaline earth metal salts thereof.

5,10,11,11a-Tetrahydro-10-acetyl-9-carbamyl-8-methyl-5-oxo-11-sulfino-1H-pyrrolo[2,1-c][1,4]benzodiazepin-2-acrylamide and alkali metal salts or alkaline earth metal salts thereof.

5,10,11,11a-Tetrahydro-9-hydroxy-8-methyl-5-oxo-11 sulfino-1H-pyrrolo[2,1-c][1,4]benzodiazepin-2- acrylamide and alkali metal salts or alkaline metal salts thereof.

5,10,11,11a-Tetrahydro-9-carbamyloxy-8-methyl5-oxo-11-sulfino-1H-pyrrolo[2,1-c][1,4]benzodiazepin-2-acrylamide and alkali metal salts or alkaline earth metal salts thereof.

5,10,11,11a-Tetrahydro-8-methyl-9-methoxycarbonyloxy -5-oxo-11-sulfo-1H-pyrrolo[2,1-c][1,4]benzodiazepin -2-acrylamide and alkali metal salts or alkaline earth metal salts thereof.

Their effective amount for controlling tumor of test animal is disclosed in U.S. Pat. No. 4,309,437 and others, and is now estimated as 0.01–0.5 mg/Kg/day for human tumor.

Thus, the benzodiazepine compound is administered parenterally as an injectable aqueous solution containing 1 to 5000 mg/l for a patient.

The solution of the present invention is made preferably at the time of use for injection by dissolving the two components in distilled water or the like. The compounds may, thus, preferably be in the form of a kit of the combination of the dry separate components which may be dissolved at the time of use. For making the solution it is advantage to dissolve the hydrogensulfite or the sulfite at first and then the benzodiazepine compound in the solution.

The injectable aqueous solution of the invention can be administered parenterally, for example intravenously. The dosage of the hydrogen sulfite or sulfite may be generally 5 to 15 times, preferably 5 to 10 times, the effective one of the benzodiazepine compound. For instance, when 2 mg of a benzodiazepine compound is to be administered, it is preferably used after dissolved in 5 ml of a physiological saline solution containing 20 mg of the hydrogensulfite or sulfite.

EXAMPLE 1

Four injectable aqueous solutions of the invention were prepared by dissolving sodium hydrogensulfite or sodium sulfite and then sodium salt of 5,10,11,11a-terahydro-9-hydroxy-8-methyl-5-oxo-11-sulfino-1H-pyrrolo[2,1-c][1,4]benzodiazepin-2-acrylamide (herein referred to simply as "Compound B") in a physiological saline solution. The concentrations of each component are shown in Table 1 (Medicine Nos. 2, 3, 4 and 5).

On the other hand, there are prepared injectable aqueous solutions containing Compound B, sodium sulfite and sodium hydrogen sulfite alone, respectively, in each concentration indicated in Table 1 (Medicine No.'s 1, 6 and 7).

Using the solutions together with the physiological saline solution serving as a control (No. 8), tests for observing the tissue injury occuring when the compound B laked out of the blood vessel were conducted by subcutaneously injecting 0.1 ml each of the solutions once in the neighborhood of the ear vein of white rabbits (male, 2.0–2.3 Kg). The change of ear thickness (formation of edema) in each of the administration groups was traced and examined for one week after the administration.

TABLE 1

| Medicine No. | Compound B mg/ml | NaHSO$_3$ mg/ml | Na$_2$SO$_3$ mg/ml |
|---|---|---|---|
| 1 | 0.2 | 0 | 0 |
| 2 | 0.2 | 1.0 | 0 |
| 3 | 0.2 | 0 | 1.0 |
| 4 | 0.2 | 2.0 | 0 |
| 5 | 0.2 | 0 | 2.0 |
| 6 | 0 | 2.0 | 0 |
| 7 | 0 | 0 | 2.0 |
| 8 | 0 | 0 | 0 |

FIG. 1 is a graph showing the local-injury controlling effect (the change of ear thickness of the rabbit) in combined administration to the ear of the rabbit of the compound B with the sulfite or hydrogensulfite. Curves 1 to 7 show respectively the effects in the administration of the preparations correspondng to the preparations Nos. 1 to 7, and the curve 8 is that for the physiological saline. The results revealed, as can be seen in FIG. 1, a statistically significant tissue-injuring controlling effect obtained by the combined use of NaHSO$_3$ or Na$_2$SO$_3$. In FIG. 1, the ratio of change of the ear thickness was expressed by the value of ratio of the increase of ear thickness after administration to the thickness just before administration at the administered site (edema ratio)

Edema ratio % =

$$\frac{\text{Ear thickness after administration} - \text{Ear thickness just before administration}}{\text{Ear thickness just before administration}} \times 100$$

EXAMPLE 2

The same materials as those in Example 1 were used to determine the effect thereof administered to white rabbits (male, 2.0–2.3 kg) in groups of four in the ear vein once a day for consective 5 days. The material administered to the respective groups was (1) physiological saline, or (2) 0.16 mg of the compound B/Kg/day, (3) 0.16 mg of the compound B+1.6 mg of NaHSO$_3$/Kg/day or (4) 1.6 mg of NaHSO$_3$/Kg/day. The solution volumes to be administered were all fixed at 0.5 ml/Kg/day which contains respective material or materials in the above dosage.

For confirmation of the effect, the appearance was observed and the thickness at the administration site was measured 4 days after the final administration to serve as the index of tissue injury.

The edema ratio was determined according to the following equation.

Edema ratio % =

$$\frac{\text{Thickness at administration site} - (A)}{\text{Thickness of ear on opposite side of medicine administration } (A)} \times 100$$

TABLE 2

| | Edema ratio (%) |
|---|---|
| 1 | 5.4 |
| 2 | 169.4 |
| 3 | 28.3 |
| 4 | 0.0 |

The results confirmed that the combined use of the benzodiazepine compound with NaHSO$_3$ exhibits a statistically significant controlling effect.

EXAMPLE 3

It was confirmed that the stability of the compound B was not affected when an aqueous solution of $NaHSO_3$ or $Na_2SO_3$ was used as the dissolving medium of the compound B. In a sample of 10 ml of an aqueous solution containing 0.2 mg of the compound B and 2.0 mg of $NaHSO_3$ or $Na_2SO_3$ in 1 ml thereof, analysis was made on high-performance liquid chromatography just after dissolving the compound B and after standing the solution for 3 hours at room temperature, to examine the stability of the compound B. The results are as shown in Table 3.

TABLE 3

|  | Ratio of remaining compound B |
|---|---|
| Compound B alone | 100% |
| Sample | 100% |

EXAMPLE 4

For confirming the antitumor activity effected by the simultaneous administration of the injectable aqueous solution of this invention, p 388 leukemia cancer-bearing $BDF_1$ mice (male, 20–22 g) were used in groups of four, to which the solution containing 0.2 mg of the compound B+2.0 mg of sodium hydrogensulfite or sodium sulfite in 1 ml thereof were administered inravenously once a day so that the dosage became as indicated in Table 4, for consecutive 4 days.

By the comparative examintion of mean survival days of the mice, index of life saving was calculated by the equation below:

$$\text{Index of life saving \%} = \frac{\text{mean survival days of the administered group} - (B)}{\text{mean survival days of the control group } (B)} \times 100$$

The results are as shown in Table 4.

TABLE 4

| Administration group of material | Mean survival day | Index of life saving (%) |
|---|---|---|
| Physiological saline (control) | 10 | 0 |
| Compound B 2 mg/Kg/day | 18.0 | 80 |
| Compound B 2 mg/Kg/day NaHSO3 20 mg/kg/day | 17.0 | 70 |
| Compound B 2 mg/Kg/day Na2SO3 20 mg/Kg/day | 17.0 | 70 |

The results showed that the antitumor activity of the compound B was not affected at all by the administration of 10 times its amount of $NaHSO_3$ or $Na_2SO_3$.

EXAMPLE 5

The materials were administered to ddY strain mice (male, 18–20 g) intravenously to determine the $LD_{50}$ (mg/Kg). The results showed taht $LD_{50}$ of the group to which the compound B alone was administered was 6.23, while that of the group to which the compound B and 10 times its amount of $NaHSO_3$ were administered in combination was 6.17, confirming that $NaHSO_3$ did not affect the acute toxicity of the compound B at all. Incidentally, $NaHSO_3$ or $Na_2SO_3$ itself is a substance prescribed in Japanese Parmacopoeia and its safety has been established already.

What is claimed is:

1. An injectable aqueous solution containing a physiologically acceptable metal hydrogensulfite and/or sulfite and an effective amount for controlling tumor of a benzodiazepine compound of the formula

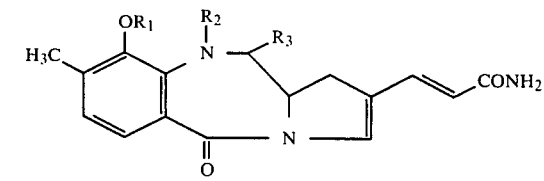

wherein $R_1$ represents a hydrogen atom, an alkanoyl group having 1 to 6 carbon atoms, a benzoyl group, a phenylcarbamyl group, an alkyl carbamyl group having 1 to 6 carbon atoms, or alkoxycarbonyl group wherein the alkoxy portion has 1 to 6 carbon atoms; $R_2$ represents a hydrogen atom, an alkanoyl group having 1 to 6 carbon atoms or a benzyl group; and $R_3$ represents a sulfinic acid residue, $SO_2X$, or sulfonic acid residue, $SO_3X$, in which X represents hydrogen, alkali metal or alkaline earth metal, wherein the amount of the hydrogensulfite and/or sulfite is 5–15 times the amount of the benzodiazepine compound.

2. The solution of claim 1, wherein the benzodiazepine compound is 5, 10, 11, 11a-tetrahydro-9-hydroxy-8-methyl-5-oxo-11-sulfino-1H-pyrrolo[2,1-c][1, 4]benzodiazepin-2-acrylamide.

3. The solution of claim 1, wherein the effective amount of the benzodiazepine compound is 1 to 5000 mg/l.

4. The solution of claim 1, wherein the physiologically acceptable metal is an alkali metal.

5. The solution of claim 4, wherein the alkali metal is sodium.

6. A pharmaceutical kit of a combination of (1) and alkali metal hydrogensulfite and/or sulfite and (2) a benzodiazepine compound of the formula

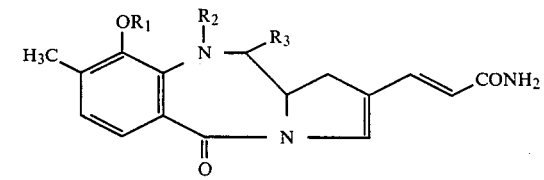

wherein $R_1$ represents a hydrogen atom, an alkanoyl group having 1 to 6 carbon atoms, a benzoyl group, a phenylcarbamyl group, an alkyl carbamyl group having 1 to 6 carbon atoms, or alkoxycarbonyl group wherein the alkoxy portion has 1 to 6 carbon atoms; $R_2$ represents a hydrogen atom, an alkanoyl group having 1 to 6 carbon atoms or a benzyl group; and $R_3$ represents a sulfinic acid residue, $SO_2X$, or sulfonic acid rest, $SO_3X$, in which X represents hydrogen, alkali metal or alkaline earth metal, wherein the amount of the hydrogensulfite and/or sulfite (1) is 5–15 times the amount of the benzodiazepine compound (2).

7. A method of controlling the occurrence of a local injury on the injection into a host animal including humans containing tumor cells of an anti-tumor benzodiazepine compound of the formula

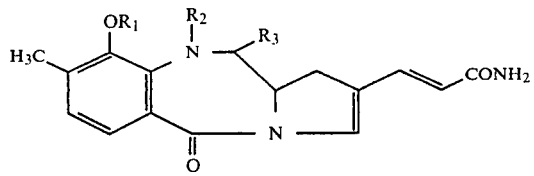

wherein $R_1$ represents a hydrogen atom, an alkanoyl group having 1 to 6 carbon atoms, a benzoyl group, a phenylcarbamyl group, an alkyl carbamyl group having 1 to 6 carbon atoms or, alkoxycarbonyl group wherein the alkoxy portion has 1 to 6 carbon atoms; $R_2$ represents a hydrogen atom, an alkanoyl group having 1 to 6 carbon atoms or a benzyl group; and $R_3$ denotes represents a sulfinic acid residue, $SO_2X$, or sulfonic acid residue, $SO_3X$, in which X represents hydrogen, alkali metal or alkaline earth metal, which method comprises injecting together with the benzodiazepine compound an alkali metal salt hydrogensulfite or sulfite in an effective amount effective to control local injury on injection in which the amount of the hydrogensulfite and/or sulfite is 5-15 times the amount of the benzodiazepine compound.

* * * * *